United States Patent [19]
Matsue et al.

[11] Patent Number: 5,866,321
[45] Date of Patent: Feb. 2, 1999

[54] ANALYTICAL METHOD AND DEVICE FOR PRECISE ANALYSIS WITH A SIMPLE SENSOR

[75] Inventors: Tomokazu Matsue; Hitoshi Shiku; Isamu Uchida, all of Miyagi, Japan

[73] Assignee: Mochida Pharmaceutical Co., Ltd., Tokyo, Japan

[21] Appl. No.: 738,114

[22] Filed: Oct. 25, 1996

[30]     Foreign Application Priority Data

Mar. 30, 1996  [JP]  Japan ..................................... 8-103948

[51] Int. Cl.⁶ ............... C12Q 1/70; C12Q 1/68; G01N 33/53; G01N 33/554
[52] U.S. Cl. ............... 435/5; 435/7.1; 435/7.21; 435/7.32; 435/6
[58] Field of Search ................. 435/5, 7.1, 7.21, 435/7.32, 6, 7.34, 7.3, 7.4, 7.92, 7.93

[56]          References Cited

U.S. PATENT DOCUMENTS 5,514,553  5/1996  Simonson .............................. 435/7.22

FOREIGN PATENT DOCUMENTS

| 0166108 | 1/1986 | European Pat. Off. . |
| 0274824 | 7/1988 | European Pat. Off. . |
| 0418384 | 11/1989 | European Pat. Off. . |
| 8166388 | 6/1996 | Japan . |
| WO9609549 | 3/1996 | WIPO . |

OTHER PUBLICATIONS

"Detection of Microspotted Carcinoembryonic Antigen on a Glass Substrate by Scanning Electrochemical Microscopy," by Hitoshi Shiku, et al; Anal. Chem, 1996, 68, 1276–1278.

"Microfabrication and Characterization of Diaphorase–Patterned Surfaces by Scanning Electrochemical Microscopy", by Hitoshi Shiku et al., Anal. Chem. 1995, 67, 312–317.

"Chemical Imaging of Surfaces with the Scanning Electrochemical Microscope", by Allen J. Bard et al., Science, vol. 254, Oct. 4, 1991, 68–74.

"Application of Scanning Electrochemical Microscopy to Biological Samples," by Chongmok Lee et al., Proc. Natl. Acad. Sci. USA, vol. 87, pp. 1740–1743, Mar. 1990.

*Primary Examiner*—Lynette F. Smith
*Attorney, Agent, or Firm*—Sughrue, Mion, Zinn, Macpeak & Seas, PLLC

[57]          ABSTRACT

An analyte and a reactant 3 that reacts with the analyte either directly or indirectly are allowed to react with each other on the analytical areas A of a substrate 1 and signals originating from the reaction are detected. In at least a signal detection step, either a signal generation-related portion 4$x$ or a detector is provided in a portion that is opposed to the substrate 1 and high and low areas are formed in either the substrate 1 or the opposed portion or both in such a manner that the distance from each analytical area A of the substrate to the opposed portion is shorter than the distance from each of the non-analytical areas B of the substrate to the opposed portion, whereby signals originating from the reaction in the analytical areas A will be detected at higher intensities than signals originating from the reaction in the non-analytical areas B. The analyte can be quantitatively or qualitatively analyzed on the analytical areas of the substrate in high precision with reduced effects from the non-analytical areas of the substrate. Simultaneous analysis of multiple samples or simultaneous analysis for multiple items can also be accomplished with a simple sensor configuration.

21 Claims, 7 Drawing Sheets

ANALYTICAL METHOD AND DEVICE FOR PRECISE ANALYSIS WITH A SIMPLE SENSOR

BACKGROUND OF THE INVENTION

This invention relates to an analytical method in which an analyte and a reactant that reacts with said analyte either directly or indirectly are allowed to react on the analytical areas of a substrate, with the resulting signals being detected for qualitative or quantitative analysis of the analyte, and in which the signals derived from the reaction on the analytical areas of the substrate are detected more intensely than those derived from the non-analytical areas, thereby allowing for higher precision in the analysis of the analyte. More specifically, the invention relates to an analytical method that employs chemical sensors, biosensors such as enzyme sensors, specific binding sensors and which enables precise analysis with a simple sensor configuration by such means as supporting the analyte on projecting analytical areas of the substrate. The invention also relates to an analytical method that enables the fabrication of miniaturized and highly precise microsensors.

Column chromatography, enzyme-chemical analyses, immunoassays and other conventional analytical methods that determine the quantities of target compounds in liquid or gaseous phase have disadvantages such as the need to use large sample volumes for analysis, the need for large analytical equipment and the prolonged time of analysis. These problems present a serious obstacle when there is a need to analyze a large number of samples simultaneously for a single analyte (i.e., simultaneous analysis of multiple samples) or when it is necessary to analyze single samples for a number of different analytical items (i.e., simultaneous analysis for multiple items).

Sensor technology has recently seen marked advances in such applications as chemical sensors, biosensors and specific binding sensors and active efforts are being made toward simplified analytical techniques and miniaturized sensing devices. However, the results are not completely satisfactory and technology is yet to be developed that uses a miniature sensor and which not only enables simultaneous analysis of multiple samples or simultaneous analysis for multiple items but also achieves high precision in these analyses.

To take one example, S. P. Fodor et al. described in Science, Vol. 251, p. 767–773 (1991) a method in which a photolithographic technique was combined with photo-sensitive protective groups to synthesize for analytical use different sequences of peptides or oligonucleotides in minute multiple regions (forming a matrix on a two-dimensional plane). P. Connolly wrote a review article in Trends Biotechnol., Vol. 12, p. 123–127 (1994) to describe a photo-fabrication process in which a lift-off technique was used to form patterns of hydrophilic and hydrophobic regions in the surface of a substrate. Similar surface processing technologies and analytical methods have been reported by C. R. Lowe et al. (U.S. Pat. No. 4,562,157), S. Nakamoto et al. (Sensors and Actuators, Vol. 13, 165 to 172 (1988), C. S. Dulcey et al. (Science, Vol. 252, 551 to 554, 1991) and S. K. Bhatia et al. [Anal. Biochem., Vol. 208, 197 to 205 (1993)].

W. T. Muller et al. described in Science, Vol. 268, p. 272–273 (1995) a process in which surface functional groups in a mono-molecular layer self-associated onto a substrate were subjected to micro-processing with a scanning probe unit such that a substance could be covalently bonded to minute regions of the substrate.

Surface processing technologies using a scanning tunnel microscope (STM) were also reported by Y. Utsugi [NATURE, Vol. 347, 747 to 749 (1990)] and P. Connolly [Nanotechnology, Vol. 2, 160 to 163 (1991)].

D. J. Pritchard et al. reported in Anal. Chim. Acta., Vol. 310, p. 251–256 (1995) a process for the fabrication of a specific binding sensor for simultaneous analysis for multiple items, which comprised reacting photo-sensitive photobiotin with each of two antibodies, with a photomask being applied to a plurality of avidin-immobilized gold electrodes on a silicon wafer substrate.

The above-mentioned micro-processing technologies are all capable of immobilizing different substances onto specified regions of a substrate. However, the fabrication process employed in these technologies includes at least several steps and hence is complicated. In addition, despite the need to process minute regions, expensive reagents such as specific binding substances (antibodies) or precious molecular recognition elements, both of which will determine the characteristics of individual sensing portions presuppose a reaction over the entire surface of the substrate, which makes the conventional technologies not always economical. What is more, the detecting regions such as electrodes must be in correct registry with the immobilized regions and, hence, a highly precise positioning technology is indispensable to the fabrication of miniature sensors. As a further problem, electrodes and other detecting portions will detect not only signals originating from the desired specific binding but also those which derive from undesired events such as the surrounding non-specific binding on the same plane and this makes the conventional technologies unsuitable for precise analyses.

In performing analyses with sensors represented by chemical sensors, biosensors such as enzyme sensors and specific binding sensors such as immunological sensors two functional parts are necessary, i.e., an analyzing part for supporting analytical reagent components such as chemical sensitive substances, bio-catalytic substances, molecular recognition elements and specific binding substances, and a detecting part for detecting signals that are generated as the result of participation of the supported substance. For achieving better precision in analysis, the precision in the amount of the substance to be supported in the analyzing part and the precision of signal detection by the detecting part must both be improved. The precision in the amount of the substance to be supported in the analyzing part depends on various factors such as the method of supporting (e.g. in a free state without being bound chemically, via covalent bonding, via non-covalent bonding, or via a specific binding substance), the precision in the quantity of reaction solution used for supporting, the precision in the quantity of the fluid to be spotted and the precision in the supporting area of the analyzing part. It should particularly be noted here that if the size of the analyzer is reduced to enable analysis of trace amount of samples, it becomes difficult to guarantee the precision in the volume of reaction solution or in the supporting area of the analyzing part. Methods so far adopted to solve these problems comprise providing minute regions of a substrate with a substance binding ability by a photolithographic technique and then bringing the entire surface of the substrate into contact with the substance to be supported. However, this approach has several disadvantages; first, the fabrication process is complicated; second, excess amounts of reagents have to be supported, which makes the approach uneconomical; third, there are unavoidable influences of non-specific adsorption onto regions where the substance of interest should not be supported or those regions to which the substance should not bind.

SUMMARY OF THE INVENTION

The present invention has been accomplished under these circumstances and has as an object providing an analytical method which comprises allowing an analyte and a reactant that reacts with said analyte either directly or indirectly to react with each other on the analytical areas of a substrate, with the resulting signals being detected for qualitative or quantitative analysis of the analyte, wherein the signals derived from the reaction on the analytical areas of the substrate are detected more intensely than those derived from the non-analytical areas, thereby enabling higher precision in the analysis of the analyte.

Another object of the invention is to enable precise analysis with a simple sensor configuration and thereby make it easy to produce a miniature and highly precise microsensor.

Yet another object of the invention is to ensure that simultaneous analysis of multiple samples or simultaneous analysis for multiple items can be performed with a trace sample volume.

The present inventors conducted intensive studies to develop a technique by which the reagent components to be analyzed were immobilized on minute regions such that they could be analyzed in a precise manner. As a result, the inventors found the following: when a reactant that would react with the analyte either directly or indirectly was immobilized on the analytical areas of a substrate and allowed to react with the analyte in an externally introduced sample or when the analyte was immobilized on the analytical areas of the substrate and allowed to react with an externally introduced reactant that would react with the analyte, with the resulting signals being detected to analyze the analyte, and in the case where a portion provided in a position opposed to the substrate was closely related to the supply of the reactant or reaction energy, signals originating from the reaction on the analytical areas could be detected intensely in a specific manner by ensuring that the distance from each analytical area of the substrate to the opposed portion is shorter than the distance from each of the non-analytical areas of the substrate to the opposed portion. The inventors also found that to ensure that the reaction occurring in the analytical areas would be detected at specifically high signal intensities, it was effective to form high and low areas, in either the substrate or the opposed portion or both. The present invention has been accomplished on the basis of these findings.

Thus, the present invention provides an analytical method which comprises allowing an analyte and a reactant that reacts with said analyte either directly or indirectly to react with each other on the analytical areas of a substrate and detecting signals originating from the reaction, wherein, at least in a signal detection step, either a signal generation-related portion that participates in the generation of said signals or a signal detection portion of said signals or both are provided in a portion that is opposed to the substrate and wherein high and low areas are formed in either the substrate or the opposed portion or both in such a manner that the distance from each analytical area of the substrate to the opposed portion is shorter than the distance from each of the non-analytical areas of the substrate to the opposed portion, whereby signals originating from said reaction in the analytical areas of the substrate will be detected at higher intensities than signals originating from the reaction in the non-analytical areas of the substrate.

In another aspect, the invention provides a substrate that has a plurality of projecting analytical areas formed thereon and which is useful in conducting the analytical method described above.

EMBODIMENTS OF THE INVENTION

Figure 1A:
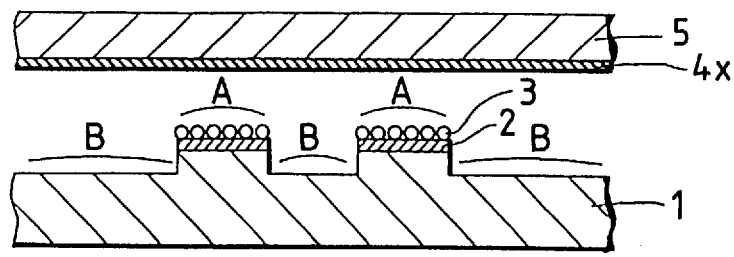
FIGS. 1A and 1B illustrate embodiments of the analytical method of the invention, respectively.

The present invention will now be described in detail.

The analytical method of the invention is such that an analyte and a reactant that reacts with said analyte either directly or indirectly are allowed to react with each other on the analytical areas of a substrate and that signals originating from the reaction are detected; the method presupposes that, in at least a signal detection step, either a portion that participates in the generation of said signals or a signal detection portion of said signals or both are provided in a portion that is opposed to the substrate. In the analytical method under consideration, the analyte, as well as the reactant that reacts with it include various substances as will be described below in detail. Other factors such as the mechanism by which signals are generated from the reaction between the analyte and the reactant, the type of signals, the manner in which the signal generation-related portion participates in the generation of signals, the type of signal detector and the site at which it is provided are also not subjected to any particular limitations and can be embodied in various ways as long as the signals originating from the above-described reaction can be specifically intensified in accordance with the relatively short distance between the opposed portion and each analytical area of the substrate.

While various substances can be reacted with the analyte in the invention, those which react directly with the analyte include (i) substances that bind directly to the analyte but which themselves will not undergo any chemical changes, and (ii) substances that bind directly to the analyte to cause chemical changes in the analyte, in themselves or in other substances.

More specifically, substances of group (i) may be exemplified by an antibody against the analyte if it is an antigen. In this case, the anti-analyte antibody is capable of direct binding to the analyte which is an antigen.

If the analyte is a nucleic acid having a specified sequence, a poly- or oligonucleotide that hybridizes complementarily with the DNA or RNA of said nucleic acid, then a specific binding substance to the analyte (to be described hereinafter), and an enzyme molecule for which the analyte is an inhibitor may be given an typical examples of the reactant of group (i). Other examples include ionically bonding substances having dissociative groups such as a carboxyl group and an amino group and hydrophobically bonding substances such as silicone.

Substances of group (ii) may be exemplified by covalent bond forming or crosslinking substances such as glutaraldehyde, carbodiimide, N-hydroxysuccinimide (NHS), disuccinidyl tartrate (DST) and N-succinimidyl-3-(2-pyridyldithio)propionate (SPDP), as well as substances having a sulfhydryl group that causes an S—S bond exchange reaction. Other examples are enzyme molecules for which the analyte is an enzyme substrate, coenzyme, cofactor, inhibitor and the like. Take, for example, the case where the analyte is glucose which is an enzyme substrate; an enzyme such as glucose oxidase (GOD) binds directly to glucose, forming D-glucono-δ-lactone and hydrogen peroxide in the presence of oxygen which is another enzyme substrate.

Substances that react indirectly with the analyte may also be used in the invention and they cause reactions that are indirectly associated with the reaction in which the analyte participates. Such substances include (a) those which bind indirectly to the analyte via a substance that binds directly to the analyte, and (b) those which do not bind to the analyte either directly or indirectly but which will bind to a substance to which the analyte binds.

Substances of group (a) include a specific binding substance to a substance that binds directly to the analyte, as exemplified by an antibody against an anti-analyte antibody. A more specific example is avidin that binds specifically to a biotin-labelled anti-analyte antibody.

Substances of group (b) may be exemplified by the same substance as the analyte or its analogs. In this case, an anti-analyte antibody is capable of binding to both the analyte and the substance of group (b), so the latter will enter into a reaction in which it competes with the analyte for the anti-analyte antibody. Another example of substances of group (b) is an enzyme that catalyzes a reaction linked with the reaction catalyzed by an enzyme capable of direct reaction with the analyte. More specifically, consider the case where the analyte is glucose and the enzyme capable of direct reaction with the analyte is GOD; the substance of group (b) in this case is peroxidase (POD) which acts on the substrate hydrogen peroxide that is generated in the GOD-catalyzed reaction.

In the present invention, the analyte and the reactant that reacts with the analyte either directly or indirectly as described above are allowed to react with each other on the analytical areas of the substrate. For this reaction, either the analyte or the reactant may be preliminarily supported on the analytical areas of the substrate whereas the reactant or the analyte is externally brought onto the analytical areas. In this case, either the analyte or the reactant may be preliminarily supported on the substrate; however, in a preferred embodiment, the reactant is preliminarily supported on the analytical areas of the substrate and then a sample for quantitative or qualitative analysis of the analyte is brought onto the analytical areas such that the reactant is reacted with the analyte; this provides a practical and useful technique for simultaneous analysis of multiple samples or simultaneous analysis for multiple items.

The manner in which the reactant is supported on the substrate is not limited to any particular embodiments as long as it is held on the analytical areas in a fashion that causes the intended reaction. Therefore, if, as in simultaneous analysis of multiple samples, sample solutions or reagent fluids are loaded onto the respective analytical areas of the substrate by dispensing or suction means such as a micro-capillary such that the sample solution or reagent fluid on one analytical area does not communicate with that on an adjacent analytical area, the reactant can be supported on the individual analytical areas in such a way that the reactant on one analytical area is isolated from the reactant on an adjacent analytical area. On the other hand, if, as in simultaneous analysis for multiple items, aliquots of a single sample solution are simultaneously distributed among the analytical areas for performing a plurality of tests, it is generally preferred to have the reactant immobilized onto the analytical areas. The immobilization of the reactant may be affected in various manners including physical adsorption on the surfaces of the analytical areas and covalent bonding to an adsorbent on the surfaces of the analytical areas. For such immobilization, one may advantageously employ those techniques which are commonly used in specific binding analyses with the aid of various solid-phase supports such as glass test tubes, plastic test tubes, porous membranes, microplates, polystyrene beads, latex particles and magnetic particles.

Signals are generated in the invention as originating from the reaction between the analyte and the reactant which reacts with it either directly or indirectly. Such signals are those which occur as the result of direct or indirect reaction between the analyte and the reactant and they are signals variable with the quantity or concentration of the analyte in a sample. Examples are: signals from an indicator by which a specific binding substance as the reactant is labelled to form a labelled specific binding substance that will participate in signal generation; signals either from a labelled specific binding substance that binds to the product of hybridizing reaction or from an intercalated substance, with the reactant being a specific binding substance of a polynucleotide sequence that hybridizes with a nucleic acid such as DNA or RNA; and signals from the product of an enzyme catalyzed reaction in which the reactant is an enzyme.

The signals under consideration include those detection signals which the skilled artisan uses in various analytical methods such as enzyme reactions, optical or electrochemical enzyme sensor methods, various immunological analyses typified by fluoroimmunoassay, enzyme immunoassay, chemiluminescence or bioluminescence immunoassay, etc. and which are known as homogeneous or heterogeneous methods, and nucleic acid amplification analyses typified by nucleic acid hybridization quantitation using a labelled antidouble-strand antibody or a fluorescent intercalator, and examples of such signals are color, emitted light such as fluorescence and electrical amounts such as current and potential. The mechanisms of signal generation in these various analytical methods may also be used as preferred cases of the invention. As in the already-described assay methods, the intensities of signals generated in the invention depend on the quantity or concentration of the analyte in samples. Therefore, the quantity or concentration of the analyte in an unknown specimen can be determined either qualitatively or quantitatively from the signal intensities detected with a suitable detector.

Specific examples of the enzyme generating signals include oxidoreductase. Examples of the oxidoreductase include oxidase (e.g., glucose oxidase and cholesterol oxidase), peroxidase (e.g., horseradish peroxidase), and dehydrogenases (e.g., diaphorase and glucose-6-phosphate dehydrogenase).

While various detectors can be used in the invention for detecting the above-described signals, a gold electrode evaporated on the substrate may typically be used if the signals to be detected are generated by an electrochemical reaction. Other detectors that can be used include carbon ink typically formed by screen printing, as well as silver paste electrodes, carbon fiber electrodes and platinum electrodes. Such electrodes may be covered with resist patterns or the like in areas that are not desirably exposed.

These electrodes may be disposed, either on the side of the substrate where the analytical areas are formed or in the portion opposed to these areas of the substrate, for use as a detector of electric current or potential. If desired, they may also be used as auxiliary electrodes. If the electrodes are to be provided in the opposed portion, the distance between the substrate and the electrode may be held constant by inserting a spacer or the like such that the substrate is laminated to the electrode in an opposed relationship with the spacer being interposed between the two.

As will be described later in the Examples, a probe electrode comprising a very thin platinum filament may also be used as a signal detector. In this case, signal detection is preferably performed with the probe electrode being actuated by precise motor drive such that it will scan over the substrate maintaining a constant distance from the substrate having the analytical areas disposed thereon. Alternatively, the substrate may be moved relative to the probe electrode for scanning.

The electrochemical detection method using the probe electrode is known as scanning electrochemical microscopy (SECM) and described in such references as C. Lee, Proc. Natl. Acad. Sci., USA, Vol. 87, p. 1740–1743 (1990), A. J. Bard at al., Science, Vol. 254, p. 68–74 (1991) and H. Shiku et al., Anal. Chem., Vol. 67, p. 312–317 (1995). The SECM can advantageously be applied for implementing the analytical method of the invention.

If the signals to be detected are light produced by fluorescence, chemiluminescence, biolumine-scence and so forth, photodetectors such as CCD and photomultiplier may be used as signal detectors.

The foregoing description of signal detectors is merely intended as illustration and should by no means be taken to imply that the method of signal detection to be employed in the invention is limited to electrochemical or optical means. The invention may adopt various methods of signal detection as long as the high and low areas formed in either the analytical areas or the reaction-related portion which is opposed to the analytical areas ensure that signals are detected in such a way that specific signals coming from the analytical areas have a clear difference in intensity from non-specific signals coming from the areas surrounding said analytical areas.

The signal generation-related portion employed in the method of invention includes such sites that, when the reaction between the analyte and the reactant which reacts with it either directly or indirectly is allowed to proceed for generating signals, the supply of a substance making a certain contribution to those phenomena or the supply of energy participating in the generation of said signals is controlled.

The control of energy supply means that the external energy required for signal generation or the external energy for promoting or suppressing signal generation is supplied in a controlled manner. The energy that participates in signal generation may be exemplified by optical and thermal energy.

When supplying energy from the signal generation-related portion, the region of energy supply is preferably restricted to the area near the surface of the signal generation-related portion such that a sufficient amount of energy will reach the analytical areas of the substrate but that the amount of energy reaching the non-analytical areas is not effective for accelerating the reaction. An example of the optical energy that can be controlled in terms of its supply region is evanescent waves which are produced on the surface of a waveguide such as a prism plate or an optical fiber. Use of the evanescent wave enables detection of a fluorophore within a thin layer. The use of optical energy has the added advantage of allowing for surface plasmid resonance (SPR) analysis utilizing the change in dielectric constant that occurs on the surface of a waveguide having an evaporated metal coating.

If the evanescent wave is to be used in the invention, the opposed portion which provides the signal generation-related portion is composed of a waveguide such as a plane prism and either the analytical areas or part of the opposed portion or both are formed as projecting regions such that the analytical areas will lie within the region to be supplied with optical energy whereas the non-analytical areas will be outside said region. Given these geometric features, a light collector installed on the side close to the substrate or the opposed portion is combined with a detector such as a photomultiplier or CCD, thereby enabling precise analysis of the signals that originate from the analytical areas.

Another example of the energy that can be employed in the invention and which can be controlled in terms of the region over which energy is supplied from the signal generation-related portion is the thermal energy controlled by a thermal cycler (as used in a DNA amplifier and so forth). By employing a thermal cycler in the invention, one can create such conditions that the temperature of the area near the heat source can be controlled to a specified level but no effective temperature control can be achieved to affect remote regions. On the other hand, nucleic acid amplifying reactions such as polymerase chain reaction (PCR) are caused by temperature circulation with a thermal cycler. Therefore, if a thermal cycler is to be used in the invention, one may cause PCR with projecting regions being formed in such a way that only the analytical areas will lie within the regions that are subject to the necessary temperature control. It should be noted here that in order to increase the temperature difference between the interior of each of said regions and its exterior, the substrate may be maintained at a constant temperature.

An embodiment of the invention using a thermal cycler will now be described more specifically below. A sequence-specific nucleotide probe is supported on the analytical areas and both a sample and any reagents such as primers and polymerases that are necessary for PCR are inserted between each analytical area and the opposed portion and, thereafter, temperature control is applied to the opposed portion by means of a thermal cycler. If the sample contains a nucleic acid sequence as the analyte, nucleic acid amplification is caused as a local phenomenon that is confined to the analytical areas. If the sample also contains a fluorescence marker that will intercalate in a double-stranded nucleic acid or an electrochemically labelled mononuclootide, the label can be incorporated into the nucleic acid amplification product. This makes it possible to detect fluorescent or electrochemical signals by a detector as a function of the amount of the product of nucleic acid amplifying reaction. Even if a component such as a nucleic acid probe is supported in areas other than the projecting analytical areas, no reaction for nucleic acid amplification will take place unless the necessary temperature control is performed. Hence, the intended assay at the analytical areas can be accomplished with high precision.

As already mentioned, the analyte and the reactant which reacts with the analyte either directly or indirectly are allowed to react with each other on the analytical areas of the substrate in the present invention and, for this reaction, either the analyte or the reactant may be preliminarily supported on the analytical areas of the substrate whereas the reactant other of the or the analyte is externally brought onto the analytical areas. Whichever of the analyte and the reactant is preliminarily supported on the analytical areas of the substrate, the signal generation-related portion may participate in signal generation in any manner and one may use various types of detectors, as well as dispose them at various sites. Stated more specifically, the signal generation-related portion may be provided in the portion opposed to the substrate and the detector provided on the other side of the substrate. Alternatively, a signal detection portion rather than the signal generation-related portion may be provided on the side close to the opposed portion. If desired, both the signal generation-related portion and the signal detecting portion may be provided on the side close to the opposed portion. If the signal generation-related portion is to be provided in the opposed portion, it may be of a type that supplies a substance participating in signal generation or it may be of a type that supplies energy. These points will now be described in detail with reference to accompanying drawings.

FIG. 1A illustrates an embodiment of the analytical method of the invention. AS shown, an insulating substrate 1 such as a silicon wafer, a glass, or a synthetic resin is provided with high and low areas in the surface. The high areas or projecting regions of the substrate 1 are provided with signal detecting electrode portions 2 each having a conductive layer formed of a semiconductor, metal, carbon ink, etc. In the embodiment under consideration, the surfaces of the signal detecting electrode portions 2 formed in the projecting regions of the insulating substrate 1 serve as analytical areas A and the recessed regions (low area) of the substrate 1 serve as non-analytical areas B. Reactant 3 that reacts with the analyte is supported on each of the signal detecting electrode portions 2 serving as analytical areas A.

A signal generation-related portion 4x is provided in a position opposed to the insulating substrate 1. The signal generation-related portion 4x may take on various forms: it may comprise a substrate 5 supporting an analytical reagent that participates in the generation of signals originating from the reaction between the analyte and the reactant 3; the signal generation-related portion 4x may function as an electrode such that an electrode reaction will take place in that portion to generate a substance that participates in the generation of signals originating from the reaction between the analyte and the reactant 3; alternatively, the signal generation-related portion 4x may be adapted such as to supply energy that participates in the generation of signals originating from the reaction between the analyte and the reactant 3.

The signal detecting electrode portions 2 supporting the reactant 3 are connected to an external detector such as a potentiostat and function as electrodes for sensing the current produced by the oxidation or reduction of the reactant 3. Such signal detecting electrode portions 2 may typically be formed by evaporation of metals such as gold or screen printing of carbon ink and so forth.

The embodiment of analytical method shown in FIG. 1A may typically be practiced in the following manner. First, a specific binding substance is supported as the reactant 3 on the projecting analytical areas A. Then, a sample solution is reacted with a horseradish peroxidase (HRP) labelled specific binding substance to form a ternary complex on the analytical areas A that consists of the binding specific substance, the analyte and the HRP labelled specific binding substance and the amount of the ternary complex depends on the concentration of the analyte in the sample solution. The HRP activity of the ternary complex is detected with each signal detecting electrode portion 2 (which functions as a detection electrode) via direct electron transfer to and from the HRP or as mediated with an electron mediator. In this case, hydrogen peroxide which is a substrate for HRP will be generated in the signal generation-related portion 4x. The signal generation-related portion 4x may be adapted to generate hydrogen peroxide by one of the following two methods: an oxidase such as glucose oxidane (GOD) is supported as an analytical reagent component on the portion 4x and glucose as well as dissolved oxygen which are substrates for GOD are subsequently introduced; or the signal generation-related portion 4x is allowed to function as an electrode which causes an electrochemical reaction to generate hydrogen peroxide.

In this setup, signals originating from the HRP activity in the ternary complex generated in the analytical areas A in accordance with the concentration of the analyte in the sample, namely, the reduction current sensed by the signal detecting electrodes 2, depends on the diffusion of the substrate for HRP from the signal generation-related portion 4x such that the intensity of the signals decreases as they depart from the portion 4x. Hence, the intensity of detection signals derived from the analyte supported on the analytical areas A which are the closer to the signal generation-related portions 4x will be less affected by such factors as the nonspecific adsorption of HRP onto undesirable regions such as the non-analytical areas B, whereby specific binding analysis can be achieved with high precision.

In the embodiment shown in FIG. 1A, high and low areas are formed on the surface of the insulating substrate 1 and signal detecting electrode portions 2 are provided in the high areas such that the surfaces of those portions will serve as projecting analytical areas A whereas the surrounding recessed regions serve as non-analytical areas B. Another embodiment of the invention is shown in FIG. 1B, in which high and low areas are formed in the signal generation-related areas 4x such that those parts of the area 4x which are opposed to the analytical areas A are located the closer to them than other areas such as non-analytical areas B.

Figure 1B:
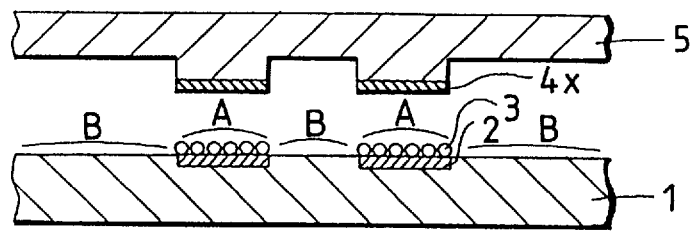

Using the analytical substrate shown in FIG. 1A or 1B, one may perform analysis by the following procedure. First, a sample containing an unknown concentration of the analyte and a HRP-labelled anti-analyte antibody are externally brought onto the analytical areas A having an anti-analyte antibody supported thereon as the reactant 3, whereupon a specific binding reaction takes place to form the aforementioned ternary complex. The sample and the HRP-labelled anti-analyte antibody may be introduced simultaneously or separately. If necessary, a washing operation may be performed between the introduction of the sample and that of the HRP-labelled anti-analyte antibody or after the formation of the ternary complex; the washing operation may typically consist of introducing a washing solution such as a buffer solution containing a surfactant and discharging the washings.

In the next step, the reagent solution necessary for signal generation, for example, an electrolyte solution containing the dissolved oxygen and glucose which are considered to be necessary when GOD is supported in the signal generation-related portion(s) 4x, is introduced between the substrate 1 and the signal generation-related portion(s) 4x, whereupon the marker enzyme HRP generates a reduction current, which is detected as a signal by the signal detecting electrode portions 2 as they are supplied with a reducing potential relative to a counter or reference electrode, with the liquid junction being formed with the electrolyte solution. The intensity of the thus detected signals depends on the amount of HRP in the ternary complex formed in the analytical areas A as a function of the concentration of the analyte in the sample. Therefore, if a standard response is obtained from the signal intensities for samples containing the analyte in known concentrations, one can determine the concentration of the analyte in the sample of interest.

In the analytical procedure described above, the specific embodiment for introducing the sample, washing solution or reagent solution is not limited to any particular manner as long as the introduced sample, washing solution or reagent solution contacts the analytical areas A of the substrate 1. In one case, the substrate 1 may be submerged in the sample or the solutions mentioned above; alternatively, the sample or the solutions may be injected into the space between the opposed elements (i.e., the signal generation-related portion (s) 4x and the substrate 1) by suitable means such as a pump or capillarity. It should, however, be noted that in a case like simultaneous analysis of multiple samples, the sample, washing solution or reagent solution is preferably dripped or spotted on specified analytical areas A by dispensing means such as a capillary to be described hereinafter.

It should also be noted that in the analytical procedure described above, the signal generation-related portions(s) 4x need not be opposed to the analytical areas A at the start of analysis but is sufficient that they are opposed to the latter at the step of signal generation. Therefore, the signal generation-related portion(s) 4x or dispensing means may be motor or otherwise driven to be movable over the substrate 1 in the X-, Y-, Z- or φ-axis, or the sample, washing solution and reagent solution may be introduced or discharged by a syringe control mechanism. In either case, the introduction of the sample, washing solution and reagent solution can be controlled by suitable means such as an external computer and the resulting increase in the latitude and precision in analysis makes an advantageous contribution to the realization of automated analysis.

Figure 2:
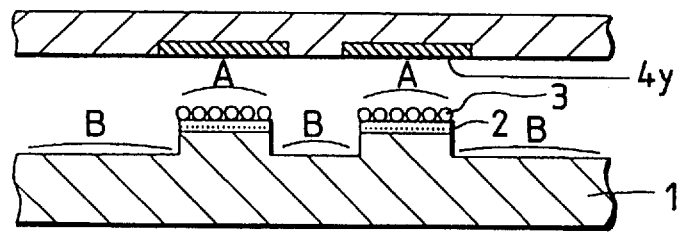
FIG. 2 illustrates another embodiment of the analytical method of the invention.

FIG. 2 illustrates yet another embodiment of the invention. As shown, an insulating substrate 1 such as a silicon wafer or a glass plate is provided with high and low areas in the surface. The high areas or projecting regions of the substrate 1 are adapted to support an analytical reagent component 3 so that those regions will serve as analytical areas A. The recessed regions surrounding the analytical areas A serve as non-analytical areas B and electrode portions 4y for detecting signals originating from the analyte are provided in positions that are opposed to the analytical areas A of the substrate 1.

A specific analytical procedure of implementing the embodiment shown in FIG. 2 may proceed as follows. First, a specific. binding substance is supported on the analytical areas A. Then, a sample solution containing the analyte is reacted with a horseradish peroxidase (HRP)-labelled specific binding substance to form a ternary complex on the analytical areas A that consists of the specific binding substance, the analyte and the HRP-labelled specific binding substance and the amount of which depends on the concentration of the analyte in the sample solution. After this specific binding reaction, the HRP activity in the ternary complex on the analytical areas A is detected with the signal detecting electrode portions 4y in the opposed area.

As in the embodiment shown in FIG. 1, hydrogen peroxide which is a substrate for HRP may be generated electrochemically or by using an oxidase such as glucose oxidase (GOD). If desired, hydrogen peroxide may be incorporated in the reaction solution. It should also be noted that an electron mediator between the HRP activity at the analytical areas A and the opposed areas 4y which function as detecting electrodes must be contained in the reaction solution.

In this setup, signals originating from the HRP activity in the ternary complex generated in the analytical areas A as a function of the concentration of the analyte in the sample, for example, values of the reduction current observed by the signal detecting electrodes, are attenuated as the distance of diffusion of the electron mediator increases and, hence, the signal intensity at the signal detecting electrode portions 4y in the opposed area will decrease as the distance between the portions 4y and the analytical area A increases. As a result, the signal representing the HRP activity in the ternary complex formed on the analytical areas A in the projecting regions can be detected in such a way that the adverse effect of HRP adsorbed nonspecifically onto the regions other than the analytical areas A, namely, the recessed non-analytical areas B surrounding the analytical areas A, can be sufficiently reduced to ensure that specific binding analysis is accomplished with high precision in the analytical areas A.

In the embodiment shown in FIG. 2, high and low areas are provided in the insulating substrate 1 such that projecting analytical areas A are surrounded with recessed non-analytical areas B. In yet another embodiment of the invention, high and low areas may be provided in the opposed area such that those portions of the opposed area which function as the signal detecting electrode portions 4y are the closer to the analytical areas A. Alternatively, the embodiment shown in FIG. 2 may be modified such that each of the analytical areas A is composed of an electrode and that a reagent component participating in signal generation is supported in the area opposed to the substrate 1.

Figure 3:
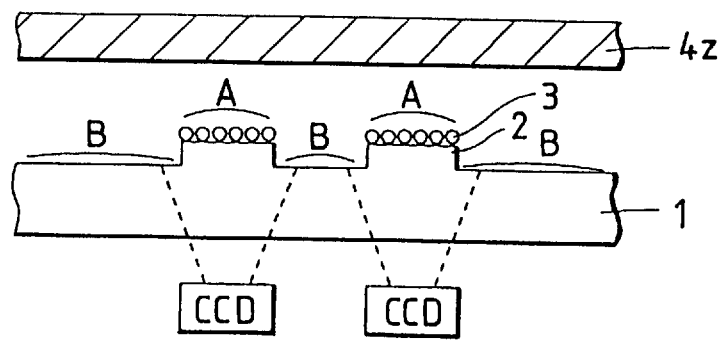
FIG. 3 illustrates yet another embodiment of the analytical method of the invention.

FIG. 3 shows a further embodiment of the invention. As shown, a transparent substrate 1 is provided with high and low areas. The high areas or projecting regions 2 which serve as analytical areas A support a reactant 3 such as a substance capable of specific binding to the analyte. An area 4z opposed to the substrate 1 is provided with a waveguide that generates evanescent waves and which thereby function as a signal generation-related portion that supplies optical energy. A plurality of CCDs are provided on the back side of the substrate 1.

Analytical procedure in this embodiment will proceed as follows. First, a sample containing the analyte and a fluorophore-labelled anti-analyte antibody are externally brought onto the analytical areas A so as to form a ternary complex there. Exemplary fluorophores include fluorescein, Texas red, phycobiliprotein, etc. In the next step, evanescent waves are generated from the opposed area 4z. Depending on the wavelength, refractive index and the incident angle of light, the extent of the evanescent waves is typically no more than about 100 nm. Therefore, in the embodiment shown in FIG. 3, the analytical areas A need be separated from the non-analytical areas B by at least 100 nm in the direction of travel of the evanescent waves so that those waves will reach the marker fluorophore binding to the surfaces of analytical areas A, which then emits fluorescence whereas the waves will not reach the marker fluorophore binding to the surfaces of non-analytical areas B, with the result that no fluorescence is emitted. Accordingly, the fluorescence from the marker fluorophore binding to the surfaces of analytical areas A can specifically be detected with the CCDs.

FIG. 3 shows the case where the signal generation-related portion for supplying optical energy is provided in the area opposed to the substrate whereas CCDs are provided as detectors on the back side of the substrate. The present invention, however, permits providing a signal detection portion on the side opposed to the substrate even if energy is to be supplied from the signal generation-related portion provided in the area opposed to the substrate. For example, the waveguide provided in the area opposed to the substrate may be so adapted that it not only supplies optical energy but also guides the fluorescence from the analytical areas into the detectors. If a thermal cycler is provided in the area opposed to the substrate, an electrode in contact with the thermal cycler may be provided as a detector in the same opposed area.

While the preferred embodiments of the invention have been described above with particular reference to accompanying drawings, it should be noted that the analytical method of the invention is by no means limited to the specified techniques set forth above. The analytical method which utilizes the HRP activity in a ternary complex as described with particular reference to FIGS. 1 and 2 (which is generally called "sandwich" specific binding analysis) is just one example of the analytical technique that can be employed in the invention and one can also apply it to competitive specific binding reactions with advantage. In addition, the present invention is advantageously applicable not only to heterogeneous assays that require washing and separating operations but also to homogeneous assays. The applicability of the invention is by no means limited to specific binding analysis and it is also applicable to chemical sensors and biosensors such as enzyme sensors.

Exemplary chemical sensors include ion-selective electrodes, gas sensors, solid electrolyte sensors, semiconductor sensors, humidity sensors, olfactory sensors and other sensors that are sensitive to chemical species in samples. These chemical sensors comprise an analyzing part which supports a substance sensitive to a chemical species of interest and a detecting part composed of a transducer such as an electrode or photoelectric device, and the chemical species is detected by sensing with the substance supported on the analyzing part.

Biosensors typically comprise an analyzing part on which an organism such as a living tissue, microorganism, cell or organelle or a biocatalytic substance such as an enzyme is supported as a molecular recognition element and a detecting part composed of a transducer such as an electrode or photoelectric device. Typical biosensors are enzyme sensors such as a glucose sensor which uses glucose oxidase (GOD) as the enzyme.

The specific binding analysis to which the invention is applicable is in no way limited to the cases shown in FIGS. 1 and 2 and it may be performed in various other embodiments. Hence, specific binding substances such as antigens, antibodies and nucleic acids such as oligonucleotides may be supported on the analyzing part, which is combined with the detecting part composed of an electrode or photoelectric device such that a specific binding reaction associated with the specific binding substance supported on the analyzing part is detected.

Thus, in the specific binding analysis, the analyte in a sample is determined qualitatively or quantitatively in association with at least one specific binding reaction between the analyte and the substance that specifically binds to it. There are many known method of the specific binding analysis, including immunoassays making use of antigen-antibody reactions, receptor assays using receptors and nucleic acid probe assays using hybridization of complementary nucleic acid sequences. Because of their specificity, these methods are commonly used in clinical testing and various other fields.

Specific examples of the analyte in the specific binding analysis include various proteins, polypeptides, glycoproteins, polysaccharides, complex glycolipids and low-molecular weight compounds that function as antibody or antigen molecules, as well as nucleic acids, effector molecules, receptor molecules, enzymes and inhibitors. More specific examples include: tumor markers such as α-fetoprotein, carcinoembryonic antibody (CEA), CA125 and CA19-9; various proteins such as $β_2$-microglobulin ($β_2$m) and ferritin; hormones such as estradiol ($E_2$), human chorionic gonadotropin (hCG), luteinizing hormone (LH) and human placental lactogen (hPL); various microorganisms such as fungi and bacteria, as,well as substances produced by the microorganisms; various virus-related antigens and antibodies such as HBs antigen, HBs antibody, HBe antigen, HBe antibody, HBc antibody, HCV antibody and HIV antibody; various allergens and IgE antibodies specific thereto; narcotic drugs, medicinal drugs and metabolites thereof, environmental markers such as pollutants, noxious substances and hazardous substances; viruses and nucleic acids of disease-related polynucleotide sequences.

The specific binding substance to be used in specific binding analysis embraces those substances which specifically bind to particular substances such as the analyte, namely, those substances which are capable of entering into reactions for specific binding to particular substances.

Therefore, the combination of the analyte and the specific binding substance therefore may be exemplified by the combination of an antigen and an antibody against it, the combination of complementary nucleic acid sequences, the combination of an effector molecule and a receptor molecule, the combination of an enzyme and an inhibitor, the combination of an enzyme and a cofactor, the combination of an enzyme and a substrate, the combination of a compound having a saccharide chain and lectin, the combination of a certain antibody and an antibody against that antibody, and the combination of a receptor molecule and an antibody against it. In these combinations, either substance can be a specific binding substance for the other substance.

Specific binding substances may be chemically modified to such an extent that their specific binding activity is not lost or they may bind with another component to form a complex substance. Such chemical modification products and complex substances are also included in the scope of "specific binding substance" in the invention and may be exemplified by antibodies or polynucleotides chemically modified with biotin, as well as antibodies covalently bonded to avidin. Other examples include antibody-enzyme or antibody-receptor fused proteins prepared by gene recombinant technology.

A practical example of sensors for implementing specific binding analysis is such that the analyte in a liquid sample is subjected to specific binding reaction with a specific binding substance, thereby forming a distance profile of a marker from the electrode portion and the value of an electric current representing the concentration of the analyte in the liquid sample and which is rate limited by the diffusion of an electron mediator is measured to determine the concentration of the analyte. This method is known as MEDIA (mediator diffusion-controlled immunoassay) and described in Unexamined Published Japanese Patent Application No. 264552/1993 (corresponding to European Patent Publication No. 0525723A2). This MEDIA method can also be used with preference in the present invention.

If the above-described analytical method of the invention is to be practiced in such an embodiment that high and low areas are provided in the substrate on which the analyte is supported, the substrate is usefully provided with a plurality of projecting analytical areas that are surrounded with recessed non-analytical areas. The substrate is particularly useful in performing specific binding analysis in the invention if a substance capable of specific binding to the analyte is supported on the projecting analytical areas.

In such substrates, the surface area of the projecting analytical areas, their height as measured from the non-analytical areas, and the distance between adjacent projecting analytical areas can be determined as appropriate for the type of the analyte and other factors; in a typical case, the height of the projecting analytical areas as measured from the non-analytical areas is adjusted to lie between 0.1 $\mu$m and 1 mm and the distance between adjacent projecting analytical areas to lie between 2 $\mu$m and 20 mm, and these dimensions will ensure that not only simultaneous analysis for multiple items but also simultaneous analysis of multiple samples can be accomplished with high precision on a routine basis.

The substrates having high and low areas of the dimensions described above can be easily fabricated by known surface processing or treating techniques such as photolithography, etching, cutting, evaporation, lamination and printing. Therefore, the analytical method of the invention has the added advantage of allowing for easy manufacture of an apparatus that is suitable for implementing the method.

The material of the substrate is not particularly limited as long as the object of the present invention can be achieved. Examples of the material of the substrate include silicon, glass, various types of synthetic and natural resins, ceramics, and the like.

If the method of the invention is to be practiced with analytical reagents supported in specified regions such as the analytical areas of the substrate, they are preferably supported in exact amounts in the specified regions in order to achieve better precision in analysis and the apparatus for implementing the method of the invention has the advantage of providing greater tolerance in the amount of the reagent to be supported and in positional precision as compared to the conventional apparatus for microanalysis. Stated more specifically, even if the reaction solution containing the analytical reagent component is applied not only to the specified regions where said reagent is to be supported but also to the surrounding areas, the intensity of signals originating from the analyte on the analytical areas of the substrate is greater than that of signals from the surrounding areas as already mentioned above, so the adverse effects which may be caused on the precision of measurement by an inaccuracy in the amount of the reagent to be supported and in the position at which it is supported can be reduced to insignificant levels. Therefore, the analytical apparatus for implementing the method of the invention can be fabricated as a high-precision microsensor.

Another advantage of the method of the invention is that unlike in the prior art case, there is no need to adopt a method by which analytical reagent components are allowed to react with the entire surface of the substrate such that they are supported in specified regions of the substrate (e.g. regions where binding functional groups have been introduced). This allows the analytical reagent to be supported on the projecting analytical areas by precise spotting with a micro-capillary, hence reducing the waste of the analytical reagent. It should also be noted that when spotting the analytical reagent by means of a micro-capillary, the latter can be sensed over the substrate as in the case of detecting signals with a probe electrode and this is preferred from the viewpoint of efficiency in the spotting operation.

Spotting with a micro-capillary offers the further advantage of enabling the formation of tiny analytical areas for simultaneous analysis for multiple items or simultaneous analysis of multiple samples and, hence, the present invention facilitates the performance of not only simultaneous analysis for multiple items but also simultaneous analysis of multiple samples. To this end, analytical areas supporting a plurality of different analytical reagents or a plurality of analytical areas onto which multiple samples or standard samples (e.g. samples of known concentrations, positive samples, negative samples and control samples) are to be spotted must be formed in tiny regions of the substrate and, according to the present invention, such analytical areas can be easily formed using a micro-capillary. In addition, a micro-capillary containing one reagent can be easily replaced by a micro-capillary containing another reagent or, alternatively, different reagents can be easily spotted with a plurality of micro-capillaries.

The following examples are provided for the purpose of further illustrating the present invention but are in no way to be-taken as limiting.

EXAMPLE 1

Simultaneous Specific minding Analysis for Multiple Items, i.e., hCG (Human Chorionic Gonadotropin) and hPL (Human Placental Lactogen), Using Specific Binding Substrate (1) Preparation of solutions A 10% HF solution was prepared by diluting 46% hydrofluoric acid (product of Morita Kagaku Kogyo Co., Ltd.) with distilled water. n-Octadecyltrichlorosilane (product of Kanto Chemical Co., Inc.) was diluted with benzene (product of Wako Pure Chemical Industries, Ltd.) to a concentration of 10 mM.

Ferrocenyl methyl alcohol (FMA) was synthesized by reducing ferrocenyl aldehyde (Product of Aldrich Chemical Company, Inc.) by the following procedure. An ethanol solution (20 mL) of ferroconyl carboxyaldehyde (product of Aldrich Chemical company, Inc.) was mixed with an ethanol solution (30 mL) containing 0.1 g of NaOH and 1.0 g of $NaBH_4$ and the mixture was refluxed for a day. Thereafter, the mixture was extracted with chloroform (50 mL) and the solvent chloroform was evaporated to yield crude FMA, which was purified by three recrystallizations with n-hexane.

A mouse monoclonal anti-hCG antibody and a mouse monoclonal anti-hPL antibody were both available from Mochida Pharmaceutical Co., Ltd. These antibodies were diluted with 0.1M phosphate buffer solution (pH, 7.0) to prepare solutions.

(2) Fabrication of analytical substrate having protecting analytical areas

Figure 4A:
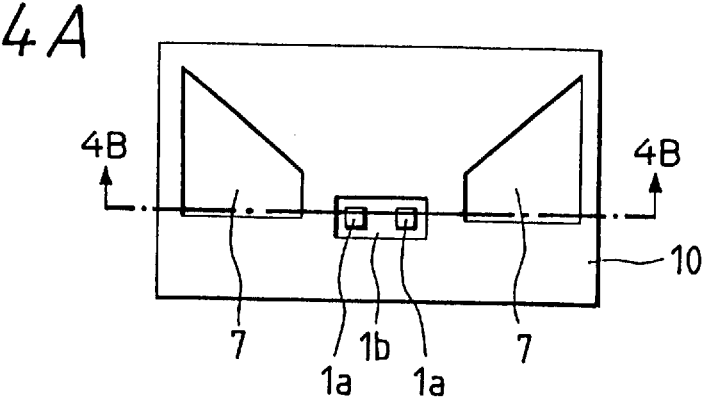
FIG. 4A is a top view of the substrate used in Example 1.
Figure 4B:
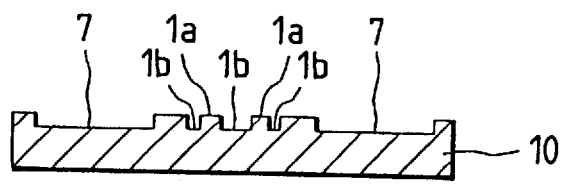
FIG. 4B is a cross section of the same substrate as in FIG. 4A.

An analytical substrate of the geometry shown in FIG. 4 at (a) (top view) and (b) (cross section) was fabricated by the following procedure. Indicated by 10, the substrate had two square (50 $\mu$m×50 $\mu$m) projecting analytical areas 1a within a rectangular (150 $\mu$m×300 $\mu$m) recessed non-analytical area 1b, as well as recessed areas 7 for positioning said analytical area.

A resist (OFPR-5000, product of Tokyo Ohka Kogyo Co., Ltd.) was spin coated onto a substrate (slide glass measuring 76 mm×26 mm×0.8 to 1.0 mm, product of Mataunami K. K.). After prebaking in an oven at 80° C. for 30 min, the resist layer was exposed to a Hg lamp (500 W) for 3 sec through a contact mask pattern. After immersion in a liquid developer for 30 sec, thorough washing with water was conducted to produce a glass substrate having a patterned resist mask. The substrate was then dipped in the 10% HF solution for 5 min to etch the unmasked exposed portions of the glass to a depth of 2 $\mu$m. As a result of this etching process, the recessed non-analytical area 1b and the recessed positioning areas 7 were formed in a depth of 2 $\mu$m, with the projecting analytical areas 1a left intact within the recessed non-analytical area 1b. The thus processed substrate was successively washed with distilled water and methanol to remove the resist, followed by another washing with distilled water and drying to produce the analytical substrate 10 having the projecting analytical areas 1a.

(3) Observation of the analytical substrate with scanning electrochemical microscope (SECM)

The substrate 10 was observed with a scanning electrochemical microscope (SECM) not only for checking the pattern of the projecting analytical areas 1a formed on substrate 10 but also for positioning the specific binding reaction area which was to be carried out on the substrate 10 in the manner to be described hereinafter.

Figure 5:
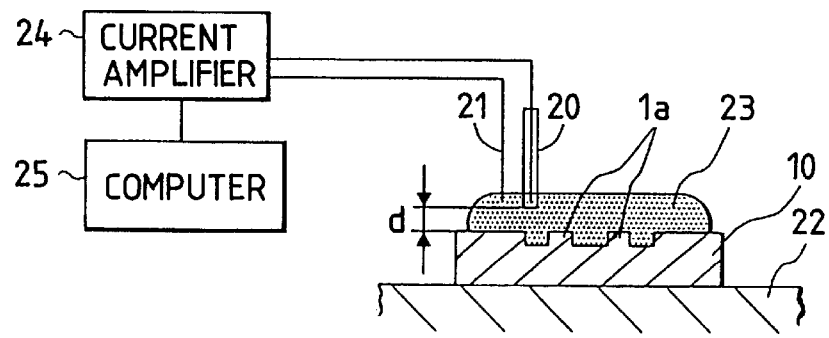
FIG. 5 illustrates the analytical method employed in Example 1.

The setup of the observing part of the SECM which was of a dual electrode type is shown in FIG. 5; the probe 20 was a micro-probe electrode (comprising a Pt electrode portion with a diameter of 5 $\mu$m encased in a glass insulator to give an overall diameter of 60 $\mu$m) and the counter electrode 21 was an electrode made of Ag—AgCl dipped in saturated potassium chloride.

The micro-probe electrode was fabricated by the following procedure. A Pt wire with a diameter of 15 $\mu$m was etched in a saturated solution of $NaNO_3$ to form a Pt filament, which was inserted into a soft glass capillary which, in turn, was fused at 320° C. in vacuo to effect glass coating. The tip of the capillary was ground with a turntable. (Model EG-6 of Narishige Scientific Instruments Laboratory) and polished with alumina particles (0.05 $\mu$m) to yield a micro-probe electrode having a circular cross section (comprising the Pt electrode portion with a diameter of 5 $\mu$m encased in the glass insulator to give an overall diameter of 60 $\mu$m).

Preliminary steps for observation with the SECM of the setup shown in FIG. 5 were as follows: the substrate 10 having the projecting analytical areas 1a which was fabricated as described in (2) was placed on top of a SECM stage 22 and an electrolyte solution 23 of the composition set forth below was dripped over the processed surface of the substrate 10 so that the latter was completely wetted with the electrolyte solution.

Composition of Electrolyte Solution for SECM 1.0 mM Ferrocenyl methyl alcohol (FMA)
 0.1M Potassium chloride
 0.1M Phosphate buffer solution (pH 7.0)

The micro-probe electrode 20 was then supplied with a potential of +400 mV vs Ag—AgCl and the distance (d) between the micro-probe electrode and the substrate 10 was held at 7 $\mu$m while SECM observation was performed at a scan speed of 9.8 $\mu$m/sec.

Scanning with the micro-probe electrode was effected on a servo-motor driven automatic XYZ stage (hereunder referred to as a "motor driven actuator"). A servomotor controller (M9103, product of Chuo Seiki K. K.) for controlling the servomotor to the automatic stage was controlled with a computer program via a GPIB bus connection. The output current was amplified with a current amplifier (Model 427, product of Keithley Instruments Inc.) and converted to a digital signal, which was sent to a computer 25 through a current amplifier 24 for measurement.

Figure 6:
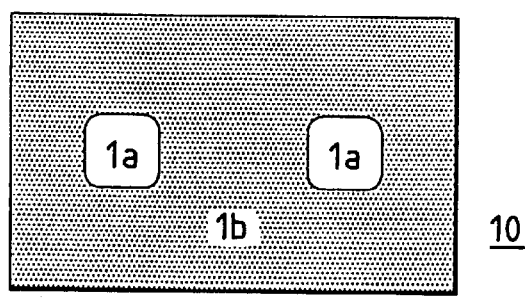
FIG. 6 is a diagrammatic representation of the SECM image of the substrate employed in Example 1.

The observed SECM image, namely, a two-dimensional profile of the oxidation current from FMA in the SECM assay solution, is shown in FIG. 6. The SECM image represents the observed current in terms of dot density and a region having the higher dot density represents an area producing the larger intensity of observed current. The substrate 10 had the analytical areas 1a projecting from the surface and when the electrode was scanning over it, the distance between the electrode and each analytical area was so small that the supply of the FMA to the electrode was blocked to reduce the current that could be picked up from the analytical areas, as clearly shown in FIG. 6. Therefore, on the basis of the SECM image shown in FIG. 6, one could not only confirm that the desired projecting analytical areas 1a and recessed non-analytical area 1b had been formed in the substrate 10 but also achieve correct positioning for scanning with the micro-probe electrode.

(4) Fabrication of specific binding substrate

Figure 7:
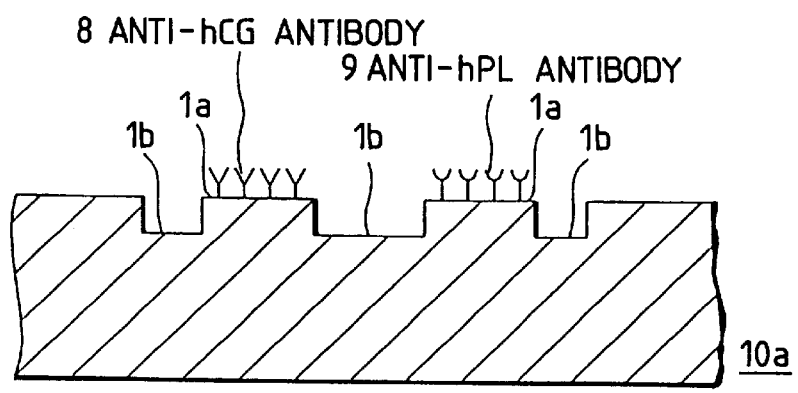
FIG. 7 is a cross section of the specific binding substrate used in Example 1.

The analytical substrate 10 having the projecting analytical areas 1 was processed as follows to fabricate a specific binding substrate suitable for use in specific binding analysis. First, the substrate 10 was rendered hydrophobic by immersion for one day in the benzene solution of n-octadecyltrichlorosilane. After drying, about 17 pL each of an anti-hCG antibody solution (760 $\mu$g/mL) and an anti-hPL antibody solution (540 $\mu$g/mL) was spotted on the respective projecting analytical areas 1a of the substrate 10 by means of glass capillary pens connected to the motor driven actuator. The substrate was then left to stand overnight, dried, and successively washed with an aqueous solution of 0.1% Tween 20 (product of Kanto Chemical Co., Inc.) and distilled water, Subsequently, the substrate 10 was submerged in an aqueous solution of bovine serum albumin (10 mg/mL, product of Wako Pure Chemical Industries, Ltd.) for 2 h to effect blocking, then washed with distilled water. In this way, both anti-hCG antibody 8 and anti-hPL antibody 9 were immobilized on the projecting analytical areas 1a of the substrate 10 and the thus fabricated specific binding substrate 10a was used in specific binding analysis as will be described below. A cross section of the specific binding substrate 10a is shown schematically in FIG. 7.

For its storage, the specific binding substrate 10a was immersed in a 0.1M phosphate buffer solution (pH 7.0) and placed under refrigerated conditions.

(5) Simultaneous specific binding analysis for multiple items, hCG and hPL, using specific binding substrate (5-1) Preparation of solutions A horseradish peroxidase (HRP) labelled mouse monoclonal anti-hCG antibody and a HRP labelled mouse monoclonal anti-hPL antibody were both available from Mochida Pharmaceutical Co., Ltd. In addition, hCG and hPL sample solutions were prepared by dilution with a 0.1M phosphate buffer solution (pH 7.0).

(5-2) Specific binding reaction

A 5-$\mu$L portion of the hCG sample solution (20 IU/mL) or hPL sample solution (1.0 $\mu$g/mL) was spotted over the specific binding substrate 10a fabricated in (4), whereby the projecting analytical areas 1a and the recessed non-analytical area 1b of the specific binding substrate 10a were completely wetted with the sample solutions prepared in (5-1). After washing with distilled water, the substrate was dipped for 20 min in a labelled antibody solution containing the HRP labelled anti-hCG antibody (20 $\mu$g/mL) and the HRP labelled anti-hPL antibody (7 $\mu$g/mL) and thereafter washed with distilled water.

(6) SECM asaay of specific binding substrate

The Specific binding substrate 10a which had been subjected to the specific binding reaction described in (5-2) was observed by SECM. The method and apparatus used were generally the same as in the SECM observation of the analytical substrate 10 which was described in (3). The only difference was that the electrolyte solution contained $H_2O_2$ (substrate for HRP) according to the composition set forth below and that the probe electrode was supplied with +50 mV vs Ag—AgCl.

Composition of Electrolyte Solution for SECM 1.0 mM Ferocenyl methyl alcohol (FMA)
0.5 mM $H_2O_2$
0.1M Potassium chloride
0.1M Phosphate buffer solution (pH 7.0)

Figure 8A:
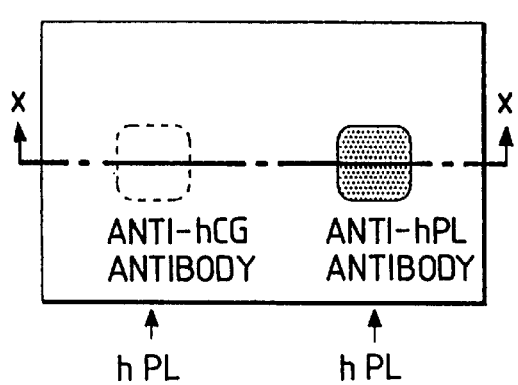
FIG. 8A is a diagrammatic representation of the SECM image taken when a hPL-containing sample solution was analyzed using the specific binding substrate.
Figure 8B:
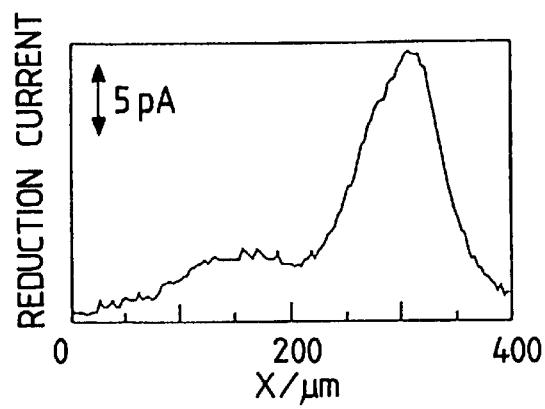
FIG. 8B is a graph showing the electric current profile obtained in the same analysis as in FIG. 8A.
Figure 9A:
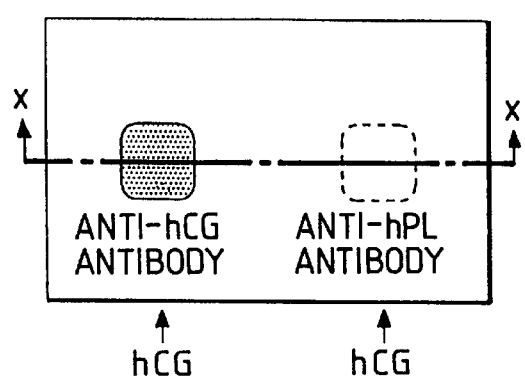
FIG. 9A is a diagrammatic representation of the SECM image taken when a hCG-containing sample solution was analyzed using the specific binding substrate.
Figure 9B:
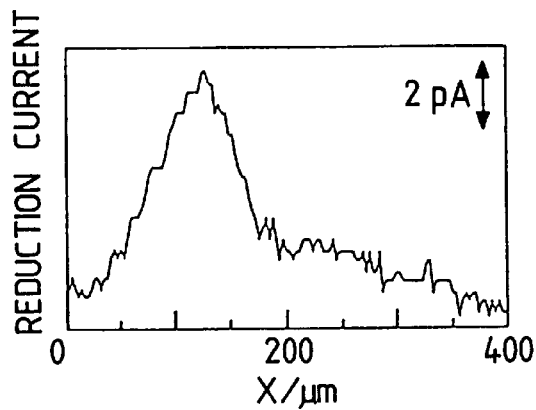
FIG. 9B is a graph showing the electric current profile obtained in the same analysis as in FIG. 9A.

When specific binding analysis was performed with the hPL sample solution prepared in (5-1), an SECM image was obtained as shown in FIG. 8A. When specific binding was performed with the hCG sample solution, an SECM image was obtained as shown in FIG. 9A. Current profiles through cross sections of FIGS. 8A and 9A as taken on line x—x are shown in FIGS. 8B and 9B, respectively.

In the projecting analytical area 1a on which the anti-hCG antibody was immobilized, the enzyme-catalyzed reduction current originating from the labelled enzyme HRP was observed only when the substrate was spotted with the hCG sample solution; on the other hand, in the projecting analytical area on which the anti-hPL antibody was immobilized, the enzyme-catalyzed reduction current originating from the labelled HRP was observed only when the substrate was spotted with the hPL sample solution. Obviously, no cross reaction had occurred between the two projecting analytical areas, one having immobilized the anti-hCG antibody 8 and the other having immobilized the anti-hPL antibody 9, within the tiny recessed non-analytical area 1b of the specific binding substrate 10a.

Figure 10:
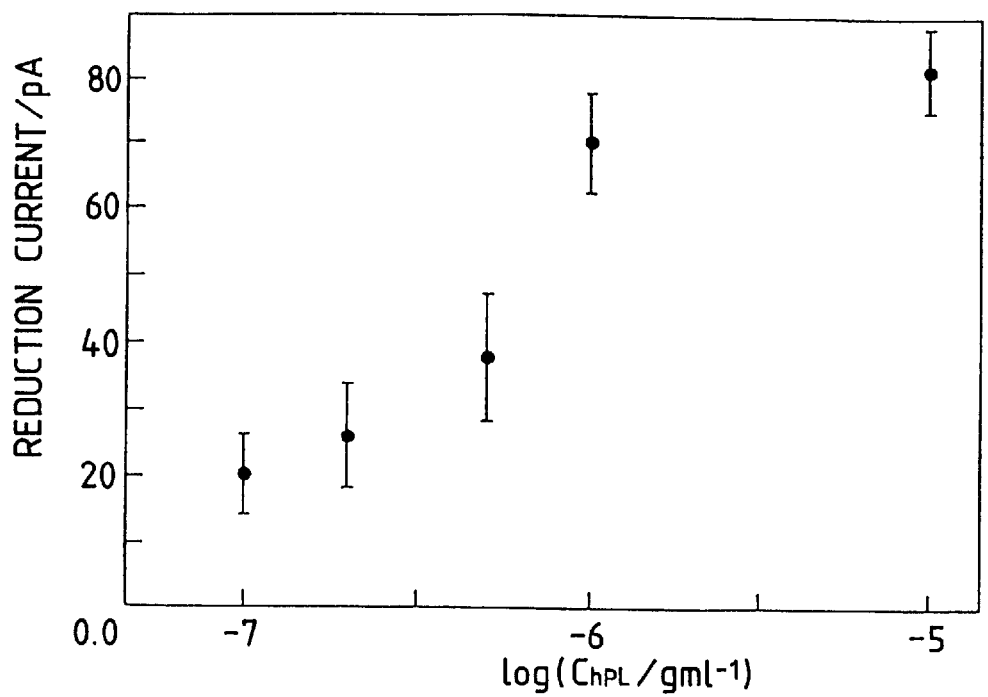
FIG. 10 is a graph showing the reduction current vs the concentration of hPL in the hPL-containing sample solution when it was analyzed using the specific binding substrate.
Figure 11:
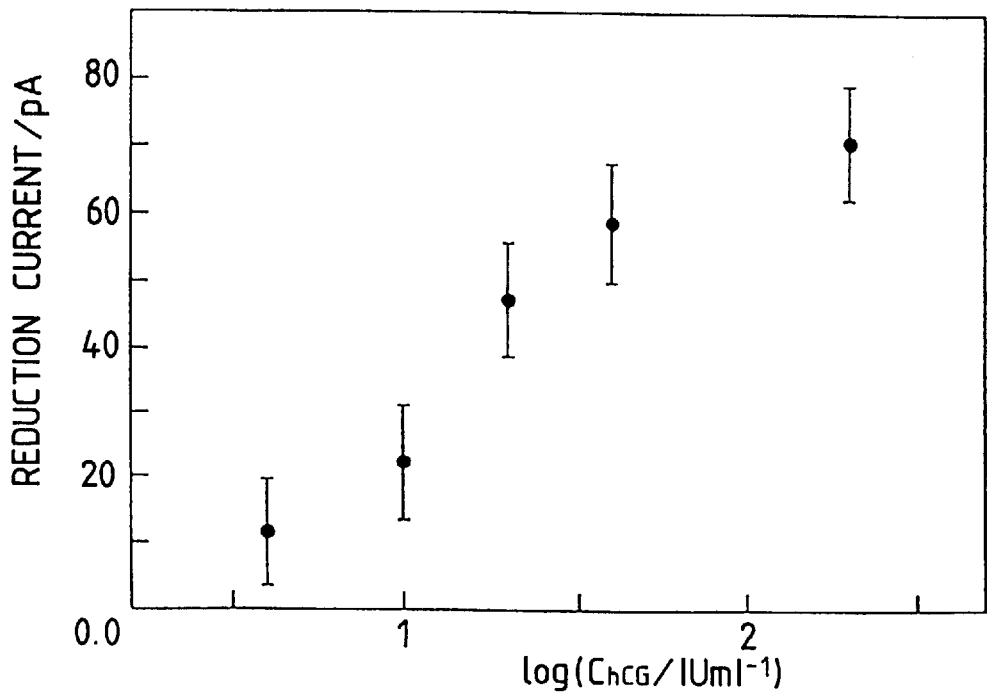
FIG. 11 is a graph showing the reduction current vs the concentration of hCG in the hCG-containing sample solution when it was analyzed using the specific binding substrate.

Similar runs of specific binding analysis were conducted with the same hPL and hCG sample solutions, except that the concentrations of hPL and hCG were varied. The relationship between the hPL concentrations and the reduction current picked up from the projecting analytical area is shown in FIG. 10, and the relationship between the hCG concentration and the reduction current picked up from the projecting analytical area is shown in FIG. 11. The two graphs show that the reduction current increased with the concentration of antigen in each sample solution. It is therefore clear that the use of the specific binding substrate fabricated in accordance with the invention permits the analyte in a sample to be analyzed quantitatively in high precision.

EXAMPLE 2

Simultaneous Specific Binding Analysis for Multiple Items, i.e., CEA (human Carcinoembryonic Antigen) and AFP (Human Alpha-Fetoprotein), Using Specific Binding Substrate (1) Preparation of Solutions A mouse monoclonal anti-CEA antibody, a mouse monoclonal anti-AEP antibody, a HRP labelled mouse monoclonal anti-CEA antibody and a RRP labelled mouse monoclonal anti-AFP antibody were all available from Mochida Pharmaceutical Co., Ltd.

Both a CEA and an AFP sample solution were prepared by dilution with a 0.1M phosphate buffer solution (pH 7.0).

(2) Preparation of specific binding substrate

An analytical substrate having projecting analytical areas was fabricated as described in Example 1 under (2). The substrate was processed as follows to fabricate a specific binding substrate. First, the analytical substrate having projecting analytical areas was rendered hydrophobic by immersion for one day in a benzene solution of n-octadecyltrichlorosilane. After drying, 20 pL each of an anti-AFP antibody solution (635 $\mu$g/mL) and an anti-CEA antibody solution (512 $\mu$g/mL) was spotted on the respective square projecting analytical areas of the substrate by means of a glass capillary connected to a motor driven actuator. The substrate was then left to stand overnight, dried and successively washed with,an aqueous solution of 0.1% Tween 20 (product of Kanto Chemical Co., Ltd.) and distilled water. Subsequently, the substrate was submerged in an aqueous solution of bovine serum albumin (10 mg/mL, product of Wako Pure Chemical Industries, Ltd.) for 2 h to effect blocking, then washed with distilled water. In this way, both the anti-AFP antibody and anti-CEA antibody were immobilized on the projecting analytical areas of the substrate and the thus fabricated specific binding substrate was used in specific binding analysis as will be described below.

For its storage, the specific binding substrate was immersed in a 0.1M phosphate buffer solution (pH 7.0) and placed under refrigerated conditions.

(3) Specific binding reaction

The specific binding substrate fabricated in (2) was spotted with 10 $\mu$L each of the AFP sample solution (50 $\mu$g/mL) or varying concentrations of the CEA sample solution ($2\times10^{-9}$, $2\times10^{-8}$, $2\times10^{-7}$, $2\times10^{-6}$, $2\times10^{-5}$ and $2\times10^{-4}$ g/mL) such that the projecting analytical areas and the recessed non-analytical area of the specific binding substrate were completely wetted with each sample solution for 1 h. After washing with distilled water, the substrate was dipped for 20 min in a labelled antibody solution containing the HRP labelled anti-AFP antibody (3.5 $\mu$g/mL) and the HRP labelled anti-CEA antibody (51 μg/mL) and thereafter washed with distilled water.

(4) SECM assay of specific binding substrate

The specific binding substrate which had been subjected to the specific binding reaction described in (3) was observed with SECM of the same setup as described in Example 1. The method was the same as described in Example 1 under (3) except that the electrolyte solution contained $H_2O_2$ (substrate for HRP) according to the composition set forth below and that the probe electrode was supplied with +50 mV vs Ag—AgCl.

Compostion of Electrolyte Solution for SECM 1.0 mM Ferocenyl methyl alcohol (FMA)

0.5 mM $H_2O_2$ 0.1M Potassium chloride 0.1M Phosphate buffer solution (pH 7.0)

Figure 12:
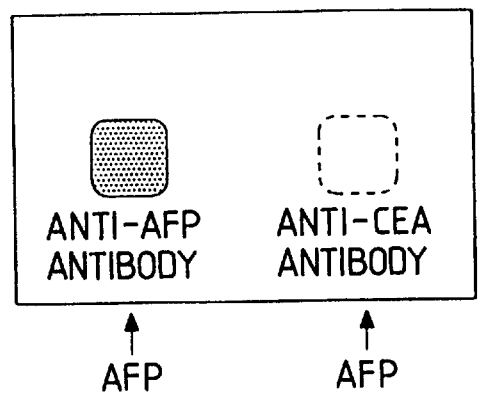
FIG. 12 is a diagrammatic representation of the SECM image taken when an AFP-containing sample solution was analyzed in Example 2 using a specific binding substrate.
Figure 13:
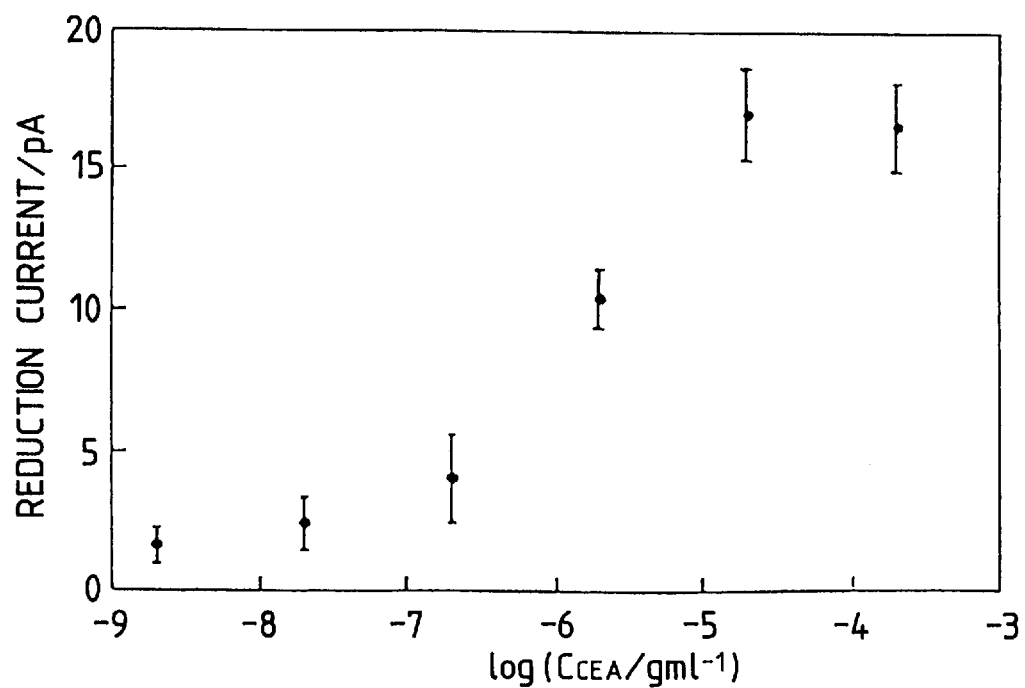
FIG. 13 is a graph showing the relationship between the CEA concentration and the SECM reduction current.

When specific binding analysis was performed with the AFP sample solution prepared in (3), an SECM image was observed as shown in FIG. 12. When specific binding analysis was performed with the varying concentrations of CEA sample solution, the reduction current could be correlated to the CEA concentration as shown in FIG. 13.

FIG. 12 shows that in the projecting analytical area on which the anti-AFP antibody was immobilized, the enzyme-catalyzed reduction current originating from the labelled enzyme HRP as observed only when the substrate was spotted with the AFP sample solution. FIG. 13 shows that the intensity of reduction current varied with the CEA concentration. It was accordingly verified that the use of the specific binding substrate fabricated in accordance with the invention permits the analyte in a sample to be analyzed quantitatively with high precision.

Comparative Example 1

Specific Binding Analysis of CEA Using Specific Binding Substrate Having No Projecting Analytical Areas (1) Preparation of samples An antibody and a HRP labelled antibody which were of the same types as used in Example 2 were employed.

Varying concentrations of CEA sample solution were prepared by dilution with a 0.1M phosphate buffer solution (pH 7.0).

(2) Fabrication of substrate having no projecting analytical areas

A substrate (slide glass) was rendered hydrophobic by immersion for 8 h in a benzene solution of n-octadecyltrichlorosilane at a concentration of 10 mM. The substrate was then immersed for 2 h in a 0.1M phosphate buffer solution (pH 7.0) containing a monoclonal anti-CEA antibody at a concentration of 500 μg/mL such that the antibody was immobilized over the entire surface of the slide glass, which was subsequently washed with distilled water and dried to fabricate an analytical substrate having no projecting analytical areas. This substrate having the antibody immobilized over the entire surface was used as a comparative specific binding substrate.

(3) Specific binding reaction

The specific binding substrate fabricated in (2) was spotted with varying concentrations ($2 \times 10^{-7}$, $2 \times 10^{-6}$, $5 \times 10^{-6}$ and $1 \times 10^{-5}$ g/mL) of CEA sample solution at intervals of 100 μm by means of a glass capillary connected to a motor driven actuator. The resulting area was found by light microscopy to have a substantially uniform size (with a radius of ca. 20 μm as produced by spotting ca. 17-pL solution). The substrate spotted with the sample solution was left to stand overnight, dried and washed with distilled water. Thereafter, the substrate was dipped for 20 min in a labelled antibody solution containing the HRP labelled anti-CEA antibody (15 μg/mL) and washed with distilled water.

(4) SECM assay of specific binding substrate

The specific binding substrate which had been subjected to the specific binding reaction described in (3) was observed with SECM of the same setup as described in Example 1. The method was the same as described in Example 1 under (3) except that the electrolyte solution contained $H_2O_2$ (substrate for HRPO) according to the formula set forth below and that the probe electrode was supplied with +50 mV vs Ag—AgCl.

Composition of Electrolyte Solution for SECM 1.0 mM Ferrocenyl methyl alcohol (FMA)

0.5 mM $H_2O_2$ 0.1M Potassium chloride 0.1M Phosphate buffer solution (pH 7.0)

Figure 14:
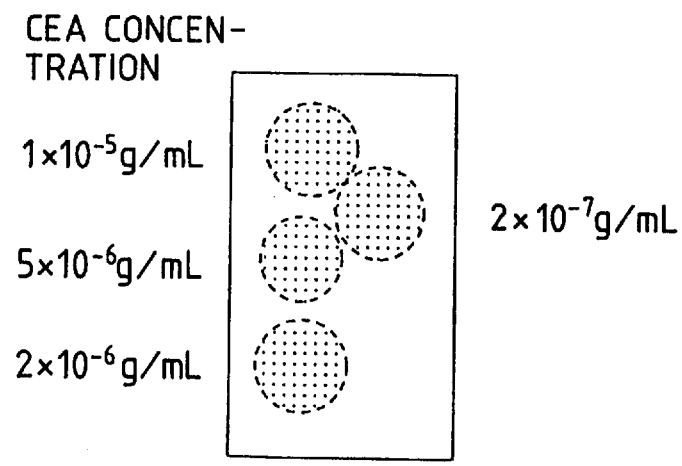
FIG. 14 is a diagrammatic representation of the SECM images taken in Comparative Example 1 using a flat substrate.
Figure 15:
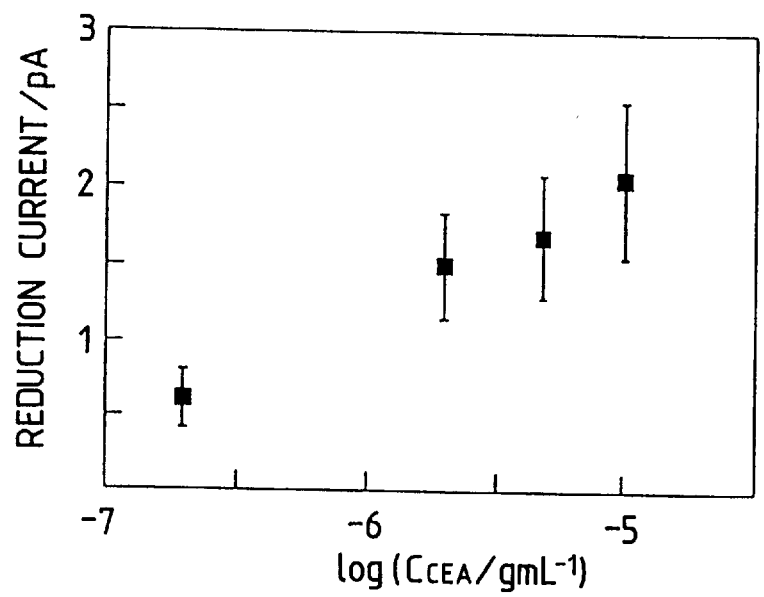
FIG. 15 is a graph showing the relationship between the CEA concentration and the SECM reduction current for Comparative Example 1 in which the flat substrate was used.

The specific binding analysis which was performed with the varying concentrations of CEA sample solution produced SECM images as shown in FIG. 14. The relationship between the reduction current picked up in SECM and the CEA concentrate is shown in FIG. 15.

FIG. 14 shows that SECM images originating from the labelled HRP were observed only in those areas of the substrate which were spotted with the sample solution. FIG. 15 shows that the intensity of reduction current varied with the CEA concentration. However, FIG. 14 also shows that the diameter of SECM images differed with the CEA concentration and that the individual images were not completely discrete. The reason would be as follows: in the comparative example, the micro-probe electrode detected all of the labelled enzyme activities on the same plane, so that the positions and boundaries of the individual analytical areas became unclear and were subject to undesired effects such as errors in the size of areas where the sample was spotted with a capillary. It is therefore concluded that the comparative substrate is not capable of enhancing the precision in analysis.

As one can see from the foregoing description, the use of the specific binding substrates having projecting analytical areas which were fabricated in Examples 1 and 2 permitted more precise analysis to be performed more easily than the comparative substrate having no projecting analytical areas, with a particular advantage being such that simultaneous analysis for items multiple (simultaneously analyzing different antibodies on adjacent projecting analytical areas) can be accomplished with high precision. In addition, the specific binding substrates fabricated in Examples 1 and 2 could reduce the amount of antibody to be used in analysis since only trace levels of antibody had to be immobilized in tiny regions of the substrate.

The analytical method of the present invention is such that when an analyte and a reactant that reacts with said analyte either directly or indirectly are allowed to react with each other on the analytical areas of a substrate, with the resulting signals being detected for qualitative or quantitative analysis of the analyte, the signals derived from the substance supported on the analytical areas are detected more intensely than those derived from the substance supported on the non-analytical areas and, hence, the analyte in the sample can be analyzed with high precision.

The method of the invention also enables precise analysis with a simple sensor configuration. The method has the added advantage that simultaneous analysis of multiple samples or simultaneous analysis for multiple items can be performed with a trace sample volume.

While the invention has been described in detail and with reference to specific embodiments thereof, it will be apparent to one skilled in the art that various changes and modifications can be made therein without departing from the spirit and scope thereof.

What is claimed is:

1. An analytical method, for qualitative or quantitative analysis of an analyte, comprising the steps of:
   (A) providing a substrate which comprises a plurality of analytical areas and non-analytical areas on a surface thereof, and a member opposed to said substrate, wherein projecting and recessed areas are provided in at least one of said substrate and said member in such a manner that the distance from each analytical area of said substrate to said member is shorter than the distance from each non-analytical area of said substrate to said member;
   (B) reacting an analyte and a reactant that reacts, either directly or indirectly, with said analyte on the analytical areas of said substrate of step (A) so as to generate signals; and
   (C) detecting said signals generated from the reaction of step (B);
   wherein, at least in detection step (C), at least one of a signal generation-related portion which participates in the generation of said signals and a signal detection portion for detecting said signals are provided in said member, and wherein signals generated from said reaction of step (B) in said analytical areas are detected at higher intensities than signals generated from a reaction in said non-analytical areas.

2. The analytical method according to claim 1, wherein in step (B) said reactant is provided on said analytical areas and a sample containing said analyte is brought into contact with said analytical areas so as to react said analyte with said reactant.

3. The analytical method according to claim 1, wherein said reactant is a substance which specifically binds to said analyte.

4. The analytical method according to claim 1, wherein said signal generation-related portion controls the supply of a signal generation-related substance that participates in the generation of said signals.

5. The analytical method according to claim 1, wherein said signal generation-related portion controls the supply of energy that participates in the generation of said signals.

6. The analytical method according to claim 5, wherein said signal generation-related portion supplies optical energy to areas near the surface of said signal generation-related portion.

7. The analytical method according to claim 5, wherein said signal generation-related portion supplies thermal energy to areas near the surface of said signal generation-related portion.

8. The analytical method according to claim 1, wherein said signal detection portion comprises a photodetector which is capable of detecting fluorescence, chemiluminescence or bioluminescence emitted by said reaction.

9. The analytical method according to claim 1, wherein said signal detection portion comprises an electrode plate or a probe electrode which is capable of detecting an electric current or potential produced by said reaction.

10. The analytical method according to claim 9, wherein said signals are detected by scanning said probe electrode over the surface of said substrate.

11. The analytical method according to claim 2, wherein at least one of the steps of providing said reactant on said analytical areas and bringing said sample containing the analyte into contact with said analytical areas, is carried out by a dispensing means which scans over the surface of said substrate.

12. The analytical method according to claim 4, wherein controlling the supply of said signal-generation-related substance is carried out by dispensing means which scans over the surface of said substrate.

13. The analytical method according to claim 3, additionally comprising the steps of washing the surface of said substrate by a dispensing means which scans over the surface of said substrate, and removing unbound analyte from the surface of said substrate by a suction means which scans over the surface of said substrate.

14. The analytical method according to claim 1, wherein said member and said substrate are separated from one another by a gap.

15. The analytical method according to claim 14, wherein said substrate and said member each have at least one planar surface.

16. The analytical method according to claim 15, wherein said at least one planar surface of said substrate is parallel to said at least one planar surface of said member.

17. The analytical method according to claim 1, wherein a signal generation-related portion is provided in said member.

18. The analytical method according to claim 1, wherein a signal detection portion is provided in said member.

19. The analytical method according to claim 1, wherein both a signal generation-related portion and a signal detection portion are provided in said member.

20. The analytical method according to claim 1, further comprising the step of:
   (D) comparing said signals detected in step (C) with signals generated from samples of analyte having known concentrations, to determine the concentration of said analyte.

21. The analytical method according to claim 1, wherein said reactant is preliminarily immobilized on said substrate before said reacting step (B).

* * * * *